United States Patent [19]
Taheri

[11] Patent Number: 6,059,824
[45] Date of Patent: May 9, 2000

[54] MATED MAIN AND COLLATERAL STENT AND METHOD FOR TREATMENT OF ARTERIAL DISEASE

[76] Inventor: Syde A. Taheri, 1275 Delaware Ave., Buffalo, N.Y. 14209

[21] Appl. No.: 09/219,044

[22] Filed: Dec. 23, 1998

[51] Int. Cl.$^7$ .................................................. A61F 2/06
[52] U.S. Cl. ................................................................ 623/1
[58] Field of Search ........................................... 623/1, 12

[56] References Cited

U.S. PATENT DOCUMENTS

| | | | |
|---|---|---|---|
| 5,755,772 | 5/1998 | Evans | 623/1 |
| 5,824,040 | 10/1998 | Cox | 623/1 |
| 5,855,598 | 1/1999 | Pinchuk | 623/1 |
| 5,906,640 | 5/1999 | Penn | 623/1 |
| 5,938,696 | 8/1999 | Goicoechea | 623/1 |

*Primary Examiner*—Michael J. Milano
*Attorney, Agent, or Firm*—Hodgson Russ Andrews Woods & Goodyear LLP

[57] ABSTRACT

The present invention is directed to the use of a stented graft having predetermined and sized lateral openings for the treatment of arterial disease at or around the intersection of multiple arteries, thereby ensuring blood flow through such arteries to collateral organs. In particular, the lateral opening of a main stent supporting a main artery has a collar with either at least two detents or inlets spaced about the annular extent thereof. The main collar mates with a collateral collar provided at the proximal end of the collateral stent having the other of at least two detents or inlets spaced about the annular extent thereof at intervals coincident with the inlets or detents on the main collar to mate and lock the main stent to the collateral stent supporting a collateral artery.

12 Claims, 4 Drawing Sheets

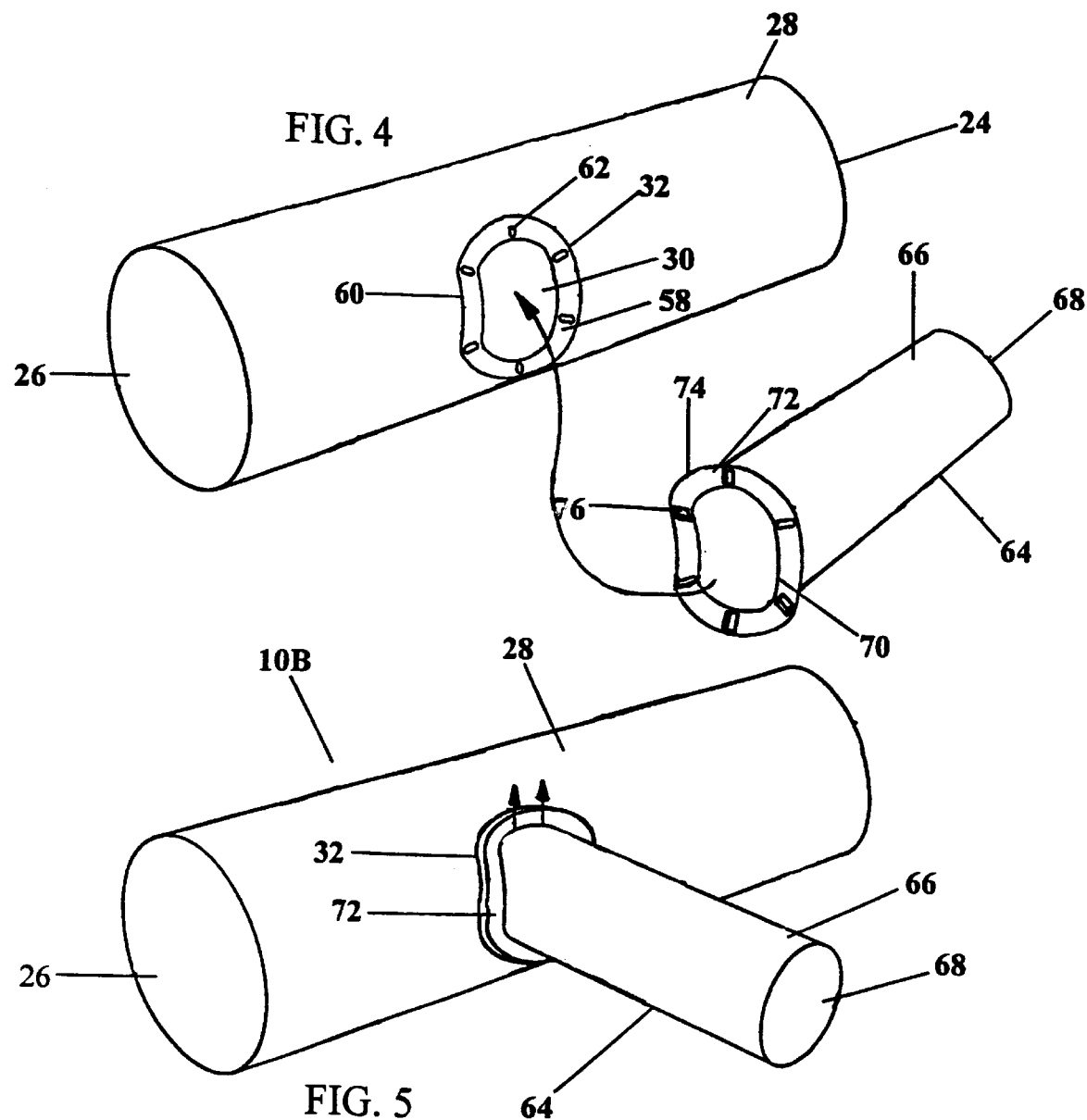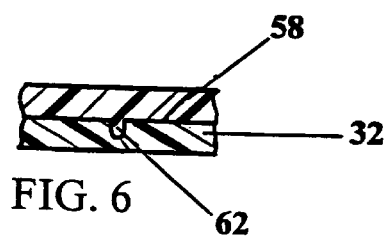

6,059,824

MATED MAIN AND COLLATERAL STENT AND METHOD FOR TREATMENT OF ARTERIAL DISEASE

BACKGROUND OF THE INVENTION

1. Field of the Invention

The present invention relates generally to the treatment of arterial disease, including for example, aortic occlusive disease, and in particular, to an improved stent assembly and method for treating arterial disease at the intersection of a plurality of arteries or blood flow passageways such as the intersection of the aorta and renal arteries or the aorta and posterior spinal arteries.

2. Prior Art

The prior art describes treatment of arterial disease by various surgical techniques, some involving the use of stents and grafts. For example, it is well known in the art to interpose within the diseased portion of an artery a stent, whether made of stainless steel, nitinol or other materials capable of being balloon-expanded, for strengthening the walls of a stenotic or occluded artery. Grafts, comprised of hollow tubes of material such as dacron, are normally inserted within the walls of a damaged artery and can be sewn into position or expanded through the use of a stented balloon catheter. It is also well known in the prior art to use a graft in conjunction with a stent to repair highly damaged portions of the aorta or other arteries thereby ensuring blood flow and reducing the risk of an aneurysm or rupture.

A more severe problem occurs when it is desirable to use a graft or a stented graft at or around the intersection of a major artery (e.g., the aorta) with intersecting collateral arteries (e.g., the renal arteries). While a stented graft is clearly preferred to strengthen and ensure the flow of blood through the aorta, the use of a stented graft effectively seals or blocks off the blood flow to collateral organs, such as the kidneys. One such technique for repairing weakened arterial walls is described in U.S. Pat. No. 5,617,878 to Taheri (Stent and Method for Treatment of Aortic Occlusive Disease). The method includes placing a graft at the intersection of two arteries. A device is used to make an opening in the graft at a point corresponding to the intersection of the two arteries. A stent is inserted into the graft and through the graft opening; the stent having a cylindrical collar with tines which grab and catch the walls of the graft to attach the stent to the opening in the graft whereby the flow of blood at the intersection of the arteries is ensured. The use of a "bifurcated" stent comprised of a single stent and graft adapted through cutting to incorporate a second stent and graft is described in U.S. Pat. No. 5,755,772 to Evans et al. The prior art techniques, while effective, have proven cumbersome and somewhat difficult to employ and execute.

The present invention solves the problems of the prior art by providing a novel and improved stent assembly and method for treating arterial disease through the use of first and second stents or first and second stented grafts mated to each other at the intersection of an occluded or diseased main artery and a collateral artery by a unique locking structure.

SUMMARY OF THE INVENTION

The present invention comprises a novel method and improved stent assembly for use in the surgical treatment of arterial disease at the intersection of at least two arteries. In particular, the present invention is directed to a novel method and improved first and second stents comprising a main graft and at least one intersecting collateral graft or, if desired, a main stented graft and at least one collateral stented graft for treating arterial disease at the intersection of various major arteries, e.g., the aorta and renal arteries or brachycephalic arteries.

The method of the present invention includes first measuring, through the use of well-known techniques such as ultrasound or other imaging, the exact location of the intersection of two arteries to be treated. The size or diameter of the artery intersection point is also measured and the lateral opening of the main graft and the open end of the collateral graft are sized so that once they are deployed and positioned in the respective main and collateral arteries, they will support the arteries at the point of intersection.

The main and collateral stents or the main and collateral stented grafts are delivered to the artery intersection location using a balloon catheter. First, the main stented graft is positioned in the main artery at the intersection of a collateral artery corresponding to a collar portion of the main stent surrounding a lateral opening thereby permitting longitudinal blood flow through the main stented graft and, as well, through the lateral opening into the intersecting collateral artery.

The main stent collar is provided with a plurality of detents or inlets at intervals spaced about the collar. The collateral stented graft is then positioned in the collateral artery with a collar at one of its open ends facing the lateral collar of the main stent such that the collateral collar opening is at the intersection of the arteries proximate the positioned main stented graft. The collar of the collateral stented graft is provided with the other of the detents and inlets at spaced intervals corresponding to that of the main stented graft. The main and collateral stented grafts are then mated to each other with the detents of one received in the inlets of the other to lock them together. When properly positioned, the mated and locked stents provide for blood flow through the main artery as well as into and through the collateral artery.

These and other aspects of the present invention will become more apparent to those of ordinary skill in the art by reference to the following description and to the appended drawings.

DESCRIPTION OF THE DRAWING FIGURES

FIG. 4 is a schematic view of the main and collateral stents of the present invention prior to being locked together.

FIG. 5 is an elevational view of the main and collateral stents shown in FIG. 4 locked together.

FIG. 6 is a cross-sectional view along line 6—6 of FIG. 5.

DESCRIPTION OF THE PREFERRED EMBODIMENT OF THE INVENTION

The present invention describes a novel method for placement of a stent assembly. More particularly, the present invention relates to mating at least two stents or stented grafts at the intersection of multiple arteries, such as the renal arteries flowing to the kidneys or the brachycephalic artery and carotid artery flowing to the brain, for use in the treatment of arterial disease at the intersection of the arteries.

The method and attendant mating stented grafts of the present invention rely upon a surgeon's ability to visualize and precisely measure the location of the intersection of diseased arteries through the use of well-known imaging techniques common in the art. Once the precise location of the intersection point and the size of the diseased arterial intersection are known, the present invention contemplates use of a first graft such as a main graft or main stented graft having coincident lateral openings adapted to be positioned at the point of artery intersection. The main lateral opening ensures that blood is capable of flowing longitudinally through the stented graft and, as well, into collateral or intersecting arteries without impediment. The present invention further includes mating a second graft such as a collateral graft or collateral stented graft having a coincident open end sized to join and locked with the main lateral opening of the first stent at the point of intersection of diseased arteries to avoid leaking or reduced blood flow.

Figure 1A:
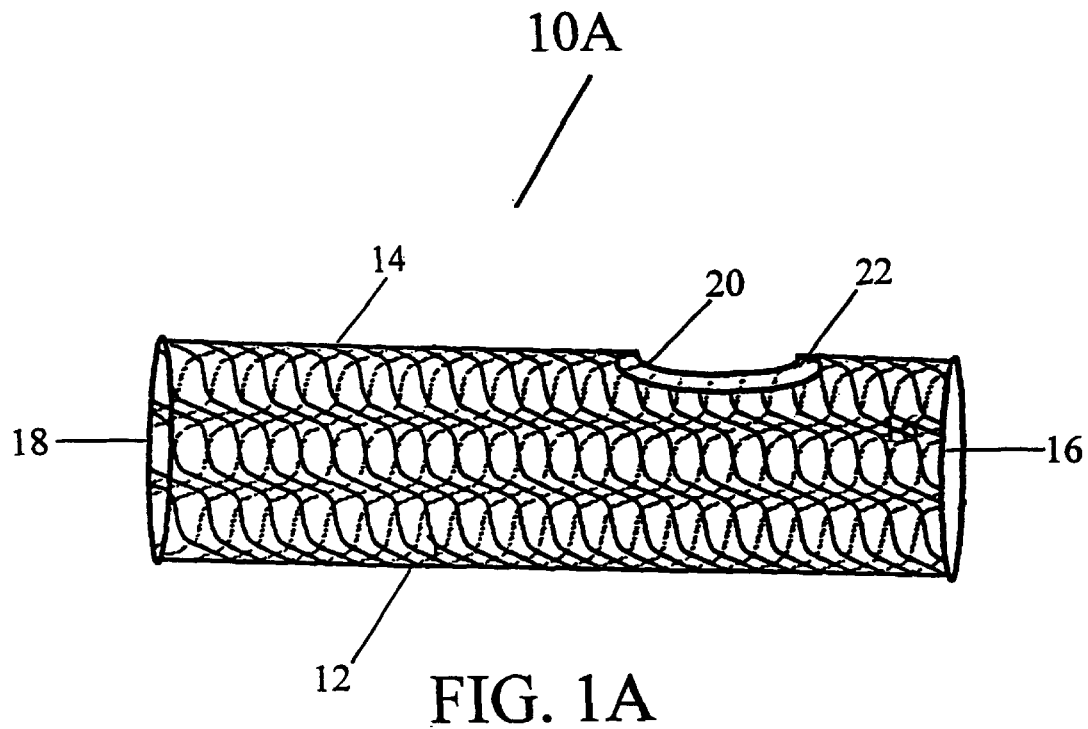
FIGS. 1A and 1B are various perspective views of the stent of the present invention generally showing the lateral openings.
Figure 1B:
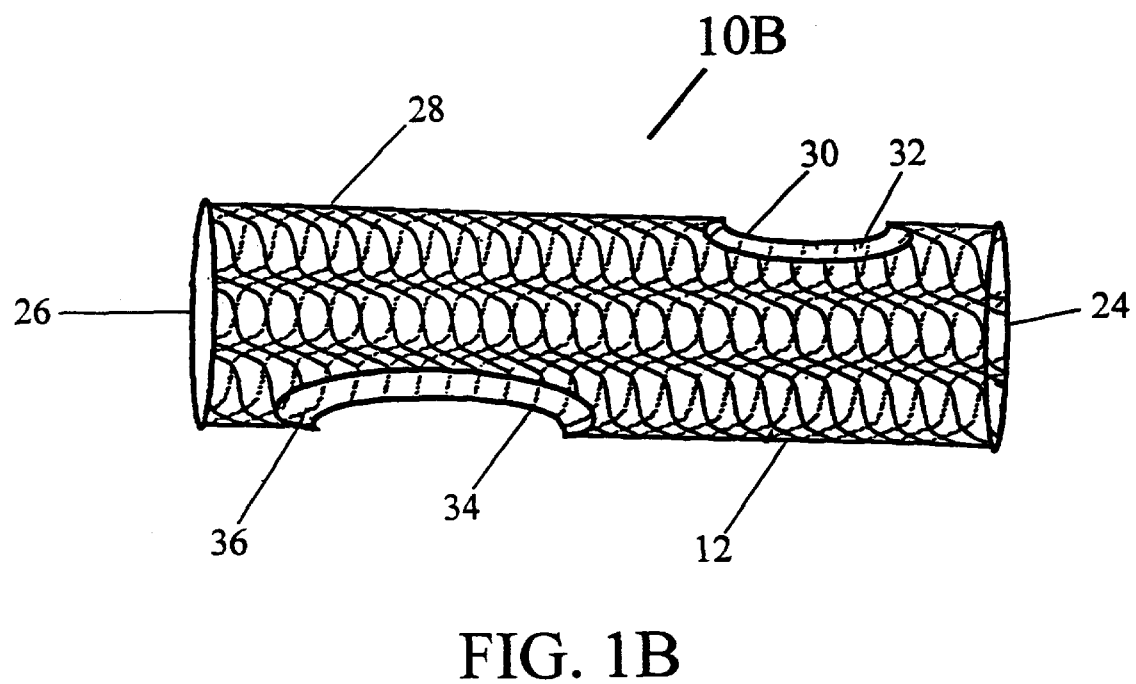

Turning now to the drawings, FIGS. 1A and 1B show various embodiments of stents 10A and 10B according to the present invention. The stents are each formed of a connecting and expandable wire mesh 12 adapted to render the stent flexible and, as well, capable of being reduced in dimension for insertion into various delivery devices such as a catheter or lumen and attendant balloon. These delivery systems are well-known in the art. Moreover, it is also well-known in the art to construct stents of various materials such as stainless steel or nitinol, capable of being reduced in size by stress or temperature and, upon delivery to a diseased artery, capable of being reformed to their original size and shape.

In particular, the stent 10A shown in FIG. 1 includes a cylindrical body portion 14 having the expandable wire mesh 12 extending to and meeting with substantially circular and opposed opening ends 16 and 18. The stent 10A also includes along its body portion 14 a substantially circular lateral opening 20 supported and defined by a lateral support collar 22. The lateral support collar 22, which can be constructed of a variety of materials (e.g., plastic, steel), serves to support and define the lateral opening 20 upon insertion of the stent 10A into an artery to be treated, as will be described in detail hereinafter.

FIG. 1B shows an alternate embodiment of a stent 10B according to the present invention. The stent 10B includes opposed openings 24 and 26 joined by a cylindrical body portion 28. The stent 10B includes a first substantially circular lateral opening 30 defined by a first lateral support collar 32 in addition to a second opening 34 defined by a second lateral support collar 36. The lateral openings 24 and 36 defined by the respective lateral collars 32, 36 are dissimilar in size.

In the stents 10A and 10B, the lateral openings are positioned along the respective stent body portions 14 and 28 at locations corresponding to the measured position of the intersection of a diseased collateral artery with a main artery to be treated. Moreover, the diameter of the various stent lateral openings together with the associated support collars are constructed to be slightly smaller than the opening of the intersecting artery communicating with the diseased main artery.

Figure 2:
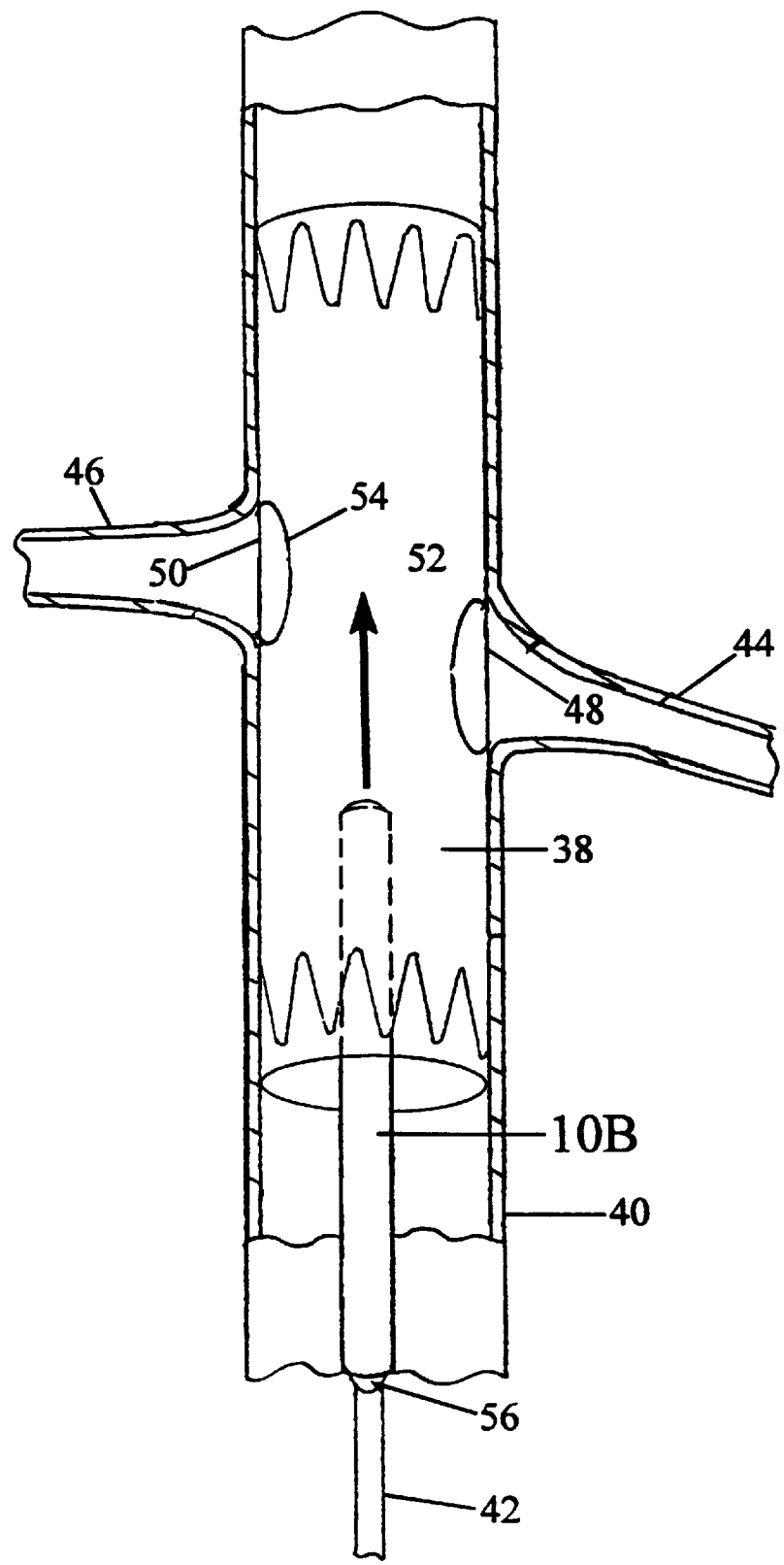
FIG. 2 is a partial cross-sectional view of the intersection of three arteries and schematically showing the introduction of a stent of the present invention received inside a graft.

As shown in FIG. 2, illustrative stent 10B in a collapsed form is adapted to fit within a graft 38 already disposed within a diseased main artery 40 by a delivery device such as a catheter/balloon assembly 42. In the drawing figure, the catheter/balloon assembly 42 is shown ready to position the stent 10B inside the graft 38. The graft 38 is positioned in the main artery at a point of intersection of two collateral arteries 44 and 46. Intersecting collateral arteries 44 and 46 have respective openings 48 and 50, each having a diameter capable of being measured with precision prior to insertion of graft 38 therein. Graft 38 includes lateral openings 52 and 54 that are positionable at locations corresponding to the location of the intersection of the collateral arteries 44 and 46 with the diseased main artery 40.

Figure 3:
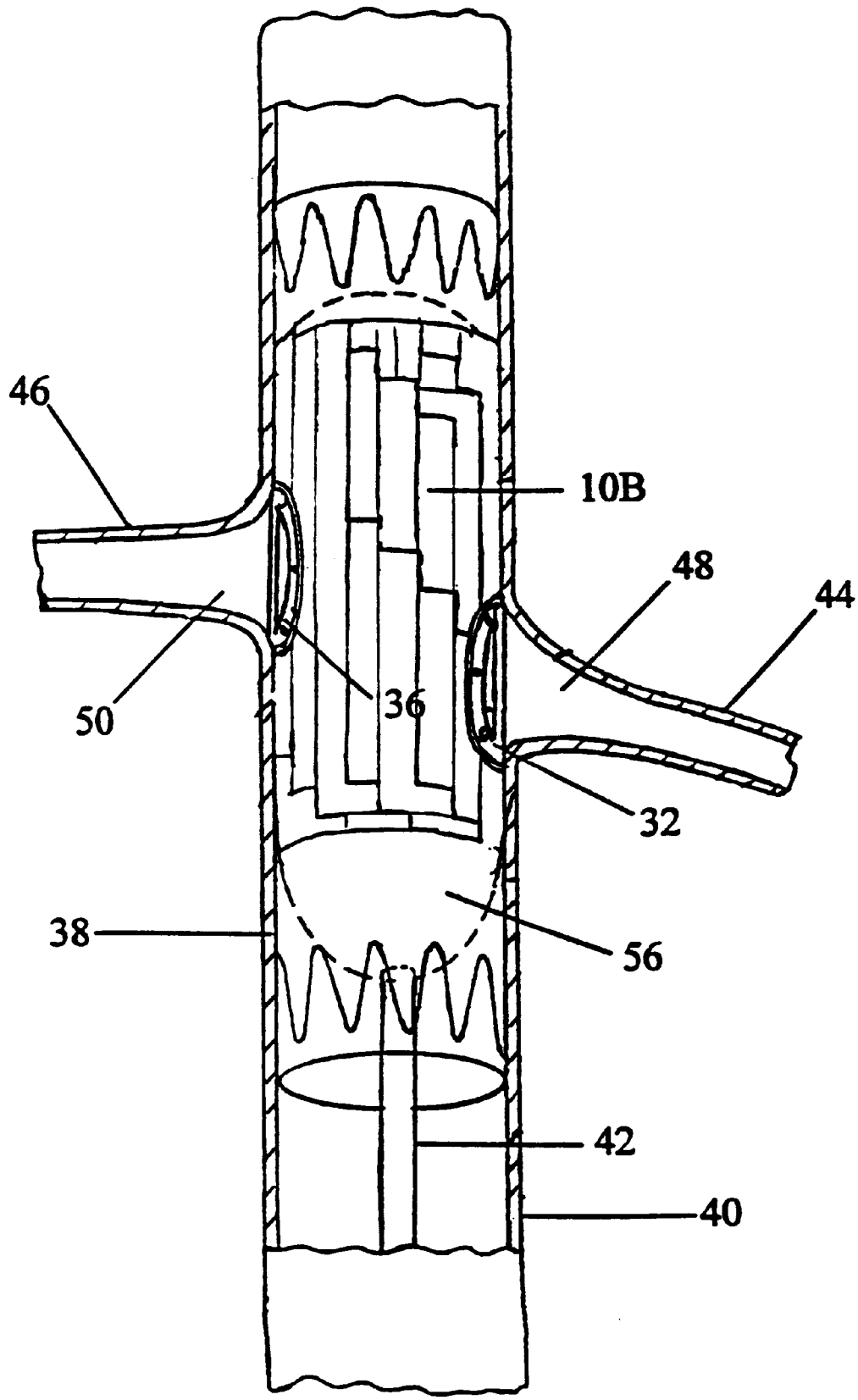
FIG. 3 is a partial sectional view of the main stented graft of the present invention interposed at the intersection of a main and collateral artery.

As shown in FIG. 3, the stent 10B is expanded against the inner wall of graft 38 by the balloon/catheter assembly 42. To that end, the physician is able to align the openings in the collapsed stent by alignment markings on the distal end of the catheter being manipulated by the physician. The expansion of stent 10B within graft 38 is only undertaken after the stent is positioned such that the lateral openings 30, 34 of the stent 10B and the lateral openings 50, 52 of the graft 38 are coincident, thereby ensuring a lateral passageway for blood flow into the collateral arteries. For example, the present stent assembly comprising the stented graft combination 18 is useful within the descending aorta at or around the intersection point of the posterior spinal arteries. The present invention is useful with aorta and kidneys communicating with intersecting renal arteries as well as general bowel and stomach arteries. The present stented graft is also useful within the aorta at or around the intersection of the cranial arteries.

In its expanded configuration, collars 32 and 36 surrounding the lateral stent openings 30 and 34 are received within the perimeter of the corresponding lateral openings 52 and 54 of the graft 38. In that position, the perimeter of the graft openings 52 and 54 surround the collars 32 and 36. An important feature of the present invention is that the collars 32, 36 are sized to be somewhat smaller than the diameter or size of the respective openings 52, 54 of the collateral arteries 44, 46 joined to the main artery 40. Further, the collars are provided with a plurality of inlets or indentations spaced about the perimeter thereof.

As shown in FIG. 4, collar 32 is provided with a relatively wide annular land portion 58 surrounding the opening 30. The land portion 58 is relatively flat and smooth in a radial direction extending outwardly from a center of the opening. However, collar 32 and land 58 are curved to accommodate the cylindrical shape of the stent body 28. This curvature is clearly shown at the area indicated as 60 in FIG. 4. The collar 32 includes at least two inlets 62 or indentations sized so that they are confined to the width of the land portion 58.

Once the graft 38 and stent 10B are properly positioned in the main artery 40 having the collars 32 and 36 aligned with the collateral arteries 44 and 46, a collateral stent 64 is mated to the main stent 10B. The collateral stent 64 is similar to the main stent 10B in terms of its materials of construction. The collateral stent 64 has a cylindrical body 66 extending to and meeting with a distal open end 68 and a proximal open end 70 provided with a collateral collar 72. The collateral collar 72 is similar to the main collar 32 in that the collateral collar has an annular land portion 74 which is relatively flat and smooth in the radial direction, but curved to seal against the land portion 58 of main collar 32. The curvature and shape of collar 72 is essentially a mirror image of collar 32. At least two detents 76 and preferably a plurality of them are sized and spaced about the annular extent of the collateral collar 72 to position, hold and lock the collateral stent 64 mated to the main stent 10B with the detents 76 received in the inlets 62 of stent 10B.

In that respect, once the graft 38 is secured in the main artery 40 by the main stent 10B, the collateral stent 64 is loaded on the catheter/balloon assembly 42, collateral collar first, and moved along a guide wire (not shown) extending through the collateral artery 44 until the collateral collar is adjacent to the main collar 32. The collateral stent 64 is rotated about its longitudinal axis to align the detents 76 with the inlets 62. This is done by rotating the catheter until markings on the manipulated end of the catheter indicate an aligned position has been achieved. The collateral stent 64 is then moved towards the main stent 10B to engage and mate the detents 76 in the inlets 62, locking the two together. The balloon 56 is deflated and the delivery assembly and guide wire are retracted from the collateral artery 44 or 46.

Those skilled in the art will readily recognize that while the present invention has been described having the main collar 32 provided with the inlets 62 and the collateral collar 74 provided with the mating detents 76, that exact configuration is not necessary to practice the present invention. For example, the collateral collar could have the inlets and the main collar the detents, or the respective collars can have both detents and inlets. What is important is that the inlets and detents are spaced about the annular extent of the respective collars at coinciding intervals and that a detent is always aligned with an inlet. Also, it is necessary that the shape and curvature of the main collar matches that of the collateral collar at least to the extent that complete annular contact is made about the annular extent between the two collars.

Accordingly, the present invention also contemplates the use of multiple stents, when required, to treat arterial disease encompassing both of two or more intersecting collateral arteries. The present invention describes a stented graft and method that can be readily adapted and used for the surgical treatment of arterial disease at or around the point of intersection of two or more arteries and clearly solves many of the problems of the prior art by allowing surgeons to employ the preferred stented graft technique in an area where such technique was not before available as an option.

Many modifications to the invention would be apparent to one of skill in the art; for example, stent configurations and grafts of various dimensions, materials and size could easily be adapted for use with the invention. Moreover, positioning of the graft and stents, critical to the success of the invention, is shown to be accomplished with the use of a balloon catheter. Other methods of positioning the stent are equally applicable without varying from the scope and purpose of the invention.

It is, therefore, appreciated that various modifications to the inventive concepts described herein may be apparent to those skilled in the art without departing from the spirit and scope of the present invention as defined by the hereinafter appended claims.

What is claimed:

1. A stent assembly for treatment of arterial disease at an intersection between a main artery and a collateral artery, which comprises:
   a) a main stent comprising a body portion adapted to be positioned in the main artery and comprising a surrounding side wall defining a passageway extending to a first opening and a second opening, wherein when the main stent is positioned in the main artery, the passageway extending to the first opening and the second opening permits the flow of blood through the main artery;
   b) at least one lateral opening provided in the surrounding side wall of the body portion of the main stent and in fluid flow communication with the passageway extending to the first opening and the second opening;
   c) a main collar surrounding and defining the one lateral opening in the body portion of the main stent, wherein the main collar has at least two first locking device provided at spaced intervals about an annular extent of the main collar sized to be somewhat less than an opening of the collateral artery aligned with the at least one lateral opening in the main stent;
   d) a collateral stent adapted to be positioned in the collateral artery and comprising a surrounding side wall defining a passageway extending to a distal opening and a proximal opening, wherein when the collateral stent is positioned in the collateral artery, the passageway extending to the distal and proximal openings permits the flow of blood through the collateral artery; and
   e) a collateral collar surrounding and defining the proximal opening of the collateral stent, wherein the collateral collar has at least two second locking device provided at spaced intervals about an annular extent of the collateral collar corresponding to the position of the first locking device provided by the main collar of the main stent such that the collateral stent is mated and locked to the main stent with the first locking device engaged with the second locking device.

2. The stent assembly of claim 1 wherein the first locking device is either a detent or an inlet, or a combination thereof, and the second locking device is the other of either a detent or an inlet, or a combination thereof.

3. A stent assembly for the treatment of arterial disease at an intersection between a main artery and a collateral artery, which comprises:
   a) a main stent comprising a body portion adapted to be positioned in the main artery and comprising a surrounding side wall defining a passageway extending to a first opening and a second opening, wherein when the main stent is positioned in the main artery, the passageway extending to the first opening and the second opening permits the flow of blood through the main artery;
   b) at least one lateral opening provided in the surrounding side wall of the body portion of the main stent and in fluid flow communication with the passageway extending to the first opening and the second opening;
   c) a main collar surrounding and defining the one lateral opening in the body portion of the main stent, wherein the main collar has at least two of either a detent or an inlet, or a combination thereof provided at spaced intervals about an annular extent of the main collar sized to be somewhat less than an opening of the collateral artery aligned with at least one lateral opening in the main stent;
   d) a collateral stent adapted to be positioned in a collateral artery and comprising a surrounding side wall defining a passageway extending to a distal opening and a proximal opening, wherein when the collateral stent is positioned in the collateral artery, the passageway extending to the distal and proximal openings permits the flow of blood through the collateral artery; and
   e) a collateral collar surrounding and defining the proximal opening of the collateral stent, wherein the collateral collar has at least two of the other of either a detent or an inlet, or a combination thereof provided at spaced intervals about an annular extent of the collateral collar corresponding to the position of the detents or inlets provided by the main collar of the collateral stent such that the collateral stent is mated and locked to the main stent with the detents of one received in the inlets of the other.

4. The stent assembly of claim 3 wherein the main and collateral stents are adapted to be selectively contracted and expanded.

5. The stent assembly of claim 3 wherein the main stent is adapted to fit within a graft and wherein the graft further comprises at least one lateral opening coincident with the one lateral opening of the main stent and wherein blood is capable of flowing through the coincident lateral openings of the main stent and graft.

6. The stent assembly of claim 3 wherein the body portion of the main stent has a cylindrical shape and the main collar has an annular land portion that is relatively flat and smooth in the radial direction and curved to contour to the cylindrical shape of the body portion.

7. The stent assembly of claim 3 wherein the body portion of the collateral stent has a cylindrical shape and the collateral collar has an annular land portion that is relatively flat and smooth in the radial direction and curved to contour to the cylindrical shape of the body portion.

8. A method for the treatment of arterial disease at an intersection between a main artery and a collateral artery, which comprises:
   a) providing a main stent comprising a body portion having a surrounding side wall defining a passageway extending to a first opening and a second opening, wherein the main stent has at least one lateral opening provided in the surrounding side wall of the body portion and in fluid flow communication with the passageway extending to the first opening and the second opening, the lateral opening defined by a main collar having at least two first locking means provided at spaced intervals about an annular extent of the main collar;
   b) positioning the main stent in the main artery supporting the arterial wall thereof with the lateral opening aligned with a collateral artery intersecting the main artery and with the main collar of the main stent sized to be somewhat less than an opening of the collateral artery aligned with the at least one collateral opening of the main stent;
   c) providing a collateral stent comprising a surrounding side wall defining a passageway extending to a distal opening and a proximal opening, wherein the collateral stent has a collateral collar surrounding and defining the proximal opening of the collateral stent and having at least two of the other of either a detent or an inlet, or a combination thereof not provided on the main collar of the main stent provided at spaced intervals about an annular extent of the collateral collar corresponding to the position of the other of the detents or inlet, or combinations thereof provided by the main collar of the main stent; and
   d) positioning the collateral stent in the collateral artery mated to the main stent with the detents of one received in the inlets of the other and the collateral stent supporting the arterial wall thereof.

9. The method of claim 8 including providing the main and collateral stents adapted to be selectively contracted and expanded.

10. The method of claim 8 including providing the main stent adapted to fit within a graft and wherein the graft further comprises at least one lateral opening coincident with the one lateral opening of the main stent and wherein blood flows through the coincident lateral openings of the main stent and graft.

11. The method of claim 8 including providing the body portion of the main stent having a cylindrical shape and the main collar having an annular land portion that is relatively flat and smooth in the radial direction and curved to contour to the cylindrical shape of the body portion.

12. The method of claim 8 including providing the body portion of the collateral stent having a cylindrical shape and the collateral collar having an annular land portion that is relatively flat and smooth in the radial direction and curved to contour to the cylindrical shape of the body portion.

* * * * *